United States Patent [19]

Perlin

[11] 4,304,240

[45] Dec. 8, 1981

[54] ESOPHAGEAL PROBE WITH DUAL SOUND DETECTION

[75] Inventor: Alfred R. Perlin, Highland Park, Ill.

[73] Assignee: The Kendall Company, Boston, Mass.

[21] Appl. No.: 128,015

[22] Filed: Mar. 7, 1980

[51] Int. Cl.³ .......................... A61B 5/02; A61B 7/04
[52] U.S. Cl. .................................... 128/671; 128/642;
128/715; 128/786; 128/773; 179/1 ST
[58] Field of Search ............. 128/642, 696, 715, 786,
128/802, 670, 349 B, 773, 671; 179/1 ST

[56] References Cited

U.S. PATENT DOCUMENTS

| | | | |
|---|---|---|---|
| 3,480,003 | 11/1969 | Crites | 128/715 X |
| 3,734,094 | 5/1973 | Calinog | 128/642 |
| 3,951,136 | 4/1976 | Wall | 128/715 X |
| 4,036,211 | 7/1977 | Veth et al. | 128/671 X |

OTHER PUBLICATIONS

Cullingford, D. W. J., *Brit. J. Anaesth*, (1964) 36, 524-526.

*Primary Examiner*—Kyle L. Howell
*Attorney, Agent, or Firm*—Powell L. Sprunger

[57] ABSTRACT

An esophageal probe comprising, an elongated hollow sleeve defining a cavity. The probe has a first vibration detection device at a first distal location in the sleeve cavity, and a second vibration detection device in the sleeve cavity, with the second detection device being spaced a substantial distance proximally from the first detection device.

7 Claims, 2 Drawing Figures

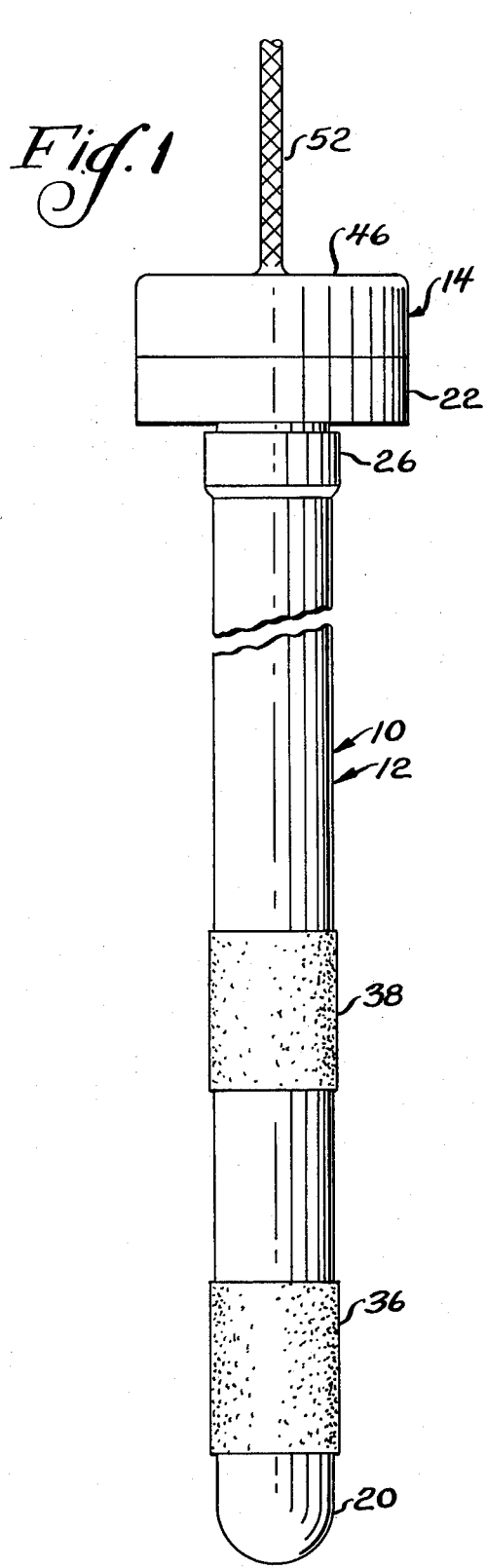
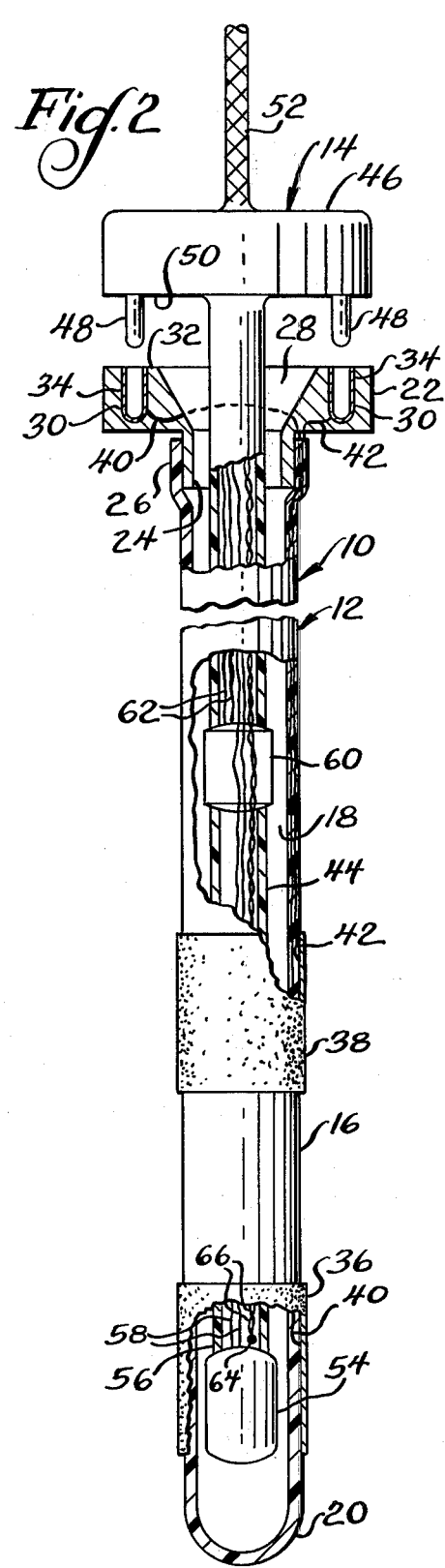

ESOPHAGEAL PROBE WITH DUAL SOUND DETECTION

BACKGROUND OF THE INVENTION

The present invention relates to esophageal probes.

Before the present invention, an assortment of esophageal probes have been proposed for detecting sounds at a single location on the probe. However, the nature of the sounds depends upon the location in the body where monitored by the probe. In the upper part of the esophagus the lung sounds of the patient are predominant while in the lower part of the esophagus near the heart the heart sounds of the patient are predominant. Thus, the prior probes are not readily adaptable to obtain both separate heart and lung sounds from the patient.

SUMMARY OF THE INVENTION

A principal feature of the present invention is the provision of an improved esophageal probe for monitoring heart and lung sounds of a patient.

The probe of the present invention comprises a disposable housing having an elongated sleeve defining a cavity. The probe has a permanent monitoring device having an elongated stem receivable in the sleeve cavity. The monitoring device has first vibration detection means at a first distal location of the stem, and second vibration detection means at a second location of the stem positioned a substantial distance proximally from the first location. The probe also has means for releasably attaching the monitoring device to the housing with the stem received in the sleeve cavity.

A feature of the present invention is that the first vibration detection means may be located in a lower part of the esophagus close to the heart when the probe is inserted into the patient for obtaining predominantly heart sounds.

Another feature of the invention is that the second vibration detection means may be located in an upper part of the esophagus in the inserted probe to obtain predominantly lung sounds.

A further feature of the invention is that the signals from the first and second vibration detection means may be suitably treated to obtain a heart sound signal and a lung sound signal.

Further features will become more fully apparent in the following description of the embodiments of this invention and from the appended claims.

DESCRIPTION OF THE DRAWINGS

In the drawings:

FIG. 1 is a fragmentary elevational view of an esophageal probe of the present invention; and FIG. 2 is a fragmentary elevational view, taken partly in section, of the probe of FIG. 1.

DESCRIPTION OF THE PREFERRED EMBODIMENTS

Referring now to FIGS. 1 and 2, there is shown an esophageal probe generally designated 10 having a disposable housing 12 and a permanent monitoring device 14. The housing 12 has an elongated hollow sleeve 16 defining a cavity 18, with the distal end 20 of the sleeve 16 being closed. The housing 12 also has an annular connector 22 having a distal annular flange 24 received in and secured to a proximal end 26 of the sleeve 16. The connector 22 has a central opening 28, and a pair of recesses 30 in a proximal face 32 of the connector 22, with sockets 34 of a conducting material, such as metal, being received in the recesses 30, as shown. The sleeve 16 and connector 22 may be made of any suitable material, such as plastic.

The sleeve 16 has a first cylindrical distal ECG electrode 36, and a second cylindrical ECG electrode 38 spaced proximally from the first electrode 36. The electrodes 36 and 38 may be made of any suitable conducting material, such as a metallic paint. The sleeve 16 has a first lead 40 connected to the electrode 36 and extending proximally in the wall of the sleeve 16 and through the connector 22 where it is connected to one of the sockets 34. The sleeve 16 also has a second lead 42 connected to the second electrode 38 and extending proximally in the sleeve wall and through the connector 22 to the other socket 34. Thus, the first and second electrodes 36 and 38 are electrically connected to the sockets 34 in the connector 22. The leads 40 and 42 may be coextruded in the sleeve wall, or the leads may be placed in a recess in the sleeve wall or may be located in the sleeve cavity 18, as desired.

The monitoring device 14 has an elongated stem 44 comprising a tube which is receivable through the connector opening 28 into the sleeve cavity 18. The monitoring device 14 also has a connector 46 connected to a proximal end of the stem 44, with a pair of conducting pins or posts 48, such as metal, extending from a distal face 50 of the connector 46, and with the pins 48 being associated with the sockets 34 of the connector 22. Thus, the connector 46 may be releasably attached to the connector 22 with the pins 48 frictionally received in the sockets 34 in a configuration with the stem 44 received in the sleeve cavity 18, and with a distal end 56 of the stem 44 located adjacent the distal end 20 of the sleeve 16. The monitoring device 14 has a pair of leads (not shown) connected to and extending from the pins 48 into a proximal cable 52. Thus, when the connector 46 is attached to the connector 22, the leads in the connector 46 and the cable 52 are electrically connected to the first and second electrodes 36 and 38 through the sockets 34 and pins 48.

The monitoring device 14 has a first vibration detection device 54, such as a microphone or hydrophone, hereinafter microphone, located at the distal end 56 of the stem 14. The monitoring device has a pair of leads 58 connected to and extending from the microphone 54 through the stem 44 and connector 46 to the cable 52. The monitoring device 14 also has a second vibration detection device 60, such as a microphone or hydrophone, hereinafter microphone, at a location of the stem 44 proximal the first microphone 54. The monitoring device 14 has a pair of leads 62 connected to and extending from the microphone 60 through the stem 44 and connector 46 to the cable 52. As shown, the second microphone 60 may be located approximately centrally between the first microphone 54 and the connector 46. The monitoring device 14 may also have a temperature sensor 64 located adjacent the distal end 56 of the stem 44 and slightly proximal the first microphone 54. The monitoring device 14 has a pair of leads 66 connected to the temperature sensor 64 and extending proximally through the stem 44 and connector 46 to the cable 52. The stem 44 and connector 46 may be made of any suitable material, such as plastic.

In use, the monitoring device 14 is attached to a housing 12 in a configuration with the pins 48 received in the sockets 34. Next, the probe 10 is positioned in the esophagus of a patient with the sleeve 16 being received in the patient and covering the monitoring device. The cable 52 of the monitoring device 14 may be connected to suitable equipment to measure the temperature of the patient through the leads connected to the temperature sensor 64, equipment to detect heart and lung sounds through the leads connected to the microphones 54 and 60, and ECG equipment to obtain an electrocardiogram through the leads electrically connected through the pins 48 and sockets 34 to the ECG electrodes 36 and 38. In the inserted configuration, the first microphone 54 is located adjacent the distal end 20 of the sleeve 16, and is located in a lower part of the esophagus in the proximity of the patient's heart, such that the first microphone 54 receives predominantly heart sounds, although the microphone 54 will also receive some lung sounds in this position. Also, in this configuration, the second microphone 60 is located in an upper part of the esophagus to receive predominantly lung sounds from the patient. Through conventional equipment, the gains of the signals from the two microphones may be adjusted, and the adjusted signal from the second microphone 60 may be substracted from the adjusted signal from the first microphone 54 to remove the contribution of the lung sounds detected by the first microphone 54, and thus obtain a signal representing pure heart sounds from the first microphone. The signal from the second microphone 60 will not contain significant heart sounds, and can be used without modification. Also, through use of a parametric or graphic equalizer, various parts of the sound spectra in the signals can be made more pronounced, as desired. For example, it may be desired to obtain solely low frequency heart sounds which are important in heart murmur diagnosis, or it may be desirable to obtain solely high frequency heart sounds which are more significant in heart valve diagnosis.

After use, the probe 10 is removed from the patient, and the disposable housing 12 is removed from the monitoring device 14. The used housing 12 may be discarded, and a new housing 12 may be connected to the monitoring device 14 for use in a subsequent patient.

The foregoing detailed description is given for clearness of understanding only, and no unnecessary limitations should be understood therefrom, as modifications will be obvious to those skilled in the art.

I claim:

1. An esophageal probe, comprising:
   an elongated hollow sleeve;
   first electrical means for detecting sounds at a first distal location in the sleeve, and a conductive lead connected to the first detecting means; and
   second electrical means for separately detecting sounds at a second location in the sleeve proximal said first location, and a conductive lead connected to the second detecting means.

2. An esophageal probe, comprising:
   an elongated hollow sleeve defining a cavity, and having a distal end, and a proximal end;
   first electrical sound detection means at a first distal location in the sleeve cavity, and a conductive lead connected to the first detection means; and
   second electrical sound detection means in the sleeve cavity, said second detection means being spaced a substantial distance proximally from the first detection means, and a conductive lead connected to the second detection means.

3. The probe of claim 2 wherein said first and second sound detection means comprise microphones.

4. The probe of claim 3 wherein the first detection means is located adjacent a distal end of the sleeve.

5. The probe of claim 3 wherein the first detection means is located in the proximity of a patient's heart when the probe is inserted into the patient.

6. An esophageal probe, comprising:
   a disposable housing having an elongated sleeve defining a cavity;
   a permanent monitoring device having an elongated stem receivable in the sleeve cavity, said monitoring device having first electrical sound detection means at a first distal location of the stem, and second electrical sound detection means at a second location of the stem positioned a substantial distance proximally from the first location; and
   means for releasably attaching the monitoring device to the housing with said stem received in the sleeve cavity.

7. The probe of claim 6 wherein the first and second detection means comprise microphones.

* * * * *